United States Patent [19]
Li

[11] Patent Number: 5,843,127
[45] Date of Patent: Dec. 1, 1998

[54] FIXATION DEVICE AND METHOD FOR INSTALLING SAME

[75] Inventor: Lehmann K. Li, Milford, Conn.

[73] Assignee: Le Medical Technologies, Inc., Shelton, Conn.

[21] Appl. No.: 426,715

[22] Filed: Apr. 21, 1995

Related U.S. Application Data

[63] Continuation-in-part of Ser. No. 294,067, Aug. 22, 1994, Pat. No. 5,645,589.

[51] Int. Cl.$^6$ .................................................. A61B 17/00
[52] U.S. Cl. ................................ 606/232; 606/73; 24/453
[58] Field of Search .............................. 606/232, 75, 68, 606/104, 73, 187; 623/13; 411/60.54; 24/453

[56] References Cited

U.S. PATENT DOCUMENTS

| | | |
|---|---|---|
| Re. 34,293 | 6/1993 | Goble et al. . |
| Re. 34,762 | 10/1994 | Goble et al. . |
| 1,247,621 | 11/1917 | Bennett . |
| 2,100,570 | 11/1937 | Saleh . |
| 2,143,086 | 1/1939 | Pleister . |
| 2,213,715 | 9/1940 | Monahan . |
| 2,453,056 | 11/1948 | Zack . |
| 2,562,419 | 7/1951 | Ferris . |
| 3,048,177 | 8/1962 | Takaro . |
| 3,143,915 | 8/1964 | Tendler . |
| 3,155,095 | 11/1964 | Brown . |
| 3,227,031 | 1/1966 | Williams . |
| 3,254,650 | 6/1966 | Collito . |
| 3,316,796 | 5/1967 | Young . |
| 4,011,602 | 3/1977 | Rybicki et al. . |
| 4,233,981 | 11/1980 | Schomacher . |
| 4,293,259 | 10/1981 | Liebig . |
| 4,379,451 | 4/1983 | Getscher ................................... 606/68 |
| 4,447,915 | 5/1984 | Weber . |
| 4,454,612 | 6/1984 | McDaniel et al. . |
| 4,501,266 | 2/1985 | McDaniel . |
| 4,525,114 | 6/1985 | Hirst . |
| 4,636,121 | 1/1987 | Miller . |
| 4,708,132 | 11/1987 | Silvestrini . |
| 4,738,255 | 4/1988 | Goble et al. . |
| 4,741,330 | 5/1988 | Hayhurst . |
| 4,744,793 | 5/1988 | Parr et al. . |
| 4,747,407 | 5/1988 | Liu et al. . |
| 4,759,765 | 7/1988 | Van Kampen . |
| 4,772,286 | 9/1988 | Goble et al. . |
| 4,776,330 | 10/1988 | Chapman et al. . |
| 4,870,957 | 10/1989 | Goble et al. . |
| 4,875,474 | 10/1989 | Border . |

(List continued on next page.)

FOREIGN PATENT DOCUMENTS

| | | |
|---|---|---|
| 1368021 | 6/1964 | France . |
| 343992 | 3/1931 | United Kingdom . |
| 9204874 | 4/1992 | WIPO . |

Primary Examiner—Jeffrey A. Schmidt
Attorney, Agent, or Firm—Ostrolenk, Faber, Gerb & Soffen, LLP

[57] ABSTRACT

A fixation device and apparatus for inserting the fixation device securely into a bore in an element, e.g. bone. The apparatus is a hand held device having an actuating mechanism and a longitudinally extending member coupled to the hand held device adapted to hold the fixation device at a distal end. The fixation device has a plurality of engaging members adapted to be moved outwardly when the fixation device is inserted into the bore to secure the fixation device in the bore. The extending member has an operating member coupled to the fixation device for exerting a force on the fixation device tending to cause the engaging members to extend outwardly to engage the wall of the bore. The operating member is releasably coupled to the fixation device so that once the fixation device is installed, the hand-held insertion apparatus can be removed. In one embodiment, the fixation device is releasably held by a forceps of the hand held device. In another embodiment, the fixation device is releasably held by a coupling member having a frangible connection adapted to break upon experiencing a preset tensile stress.

26 Claims, 7 Drawing Sheets

U.S. PATENT DOCUMENTS

| | | |
|---|---|---|
| 4,892,547 | 1/1990 | Brown . |
| 4,898,156 | 2/1990 | Gatturna . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. . |
| 4,946,468 | 8/1990 | Li . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble . |
| 4,986,263 | 1/1991 | Dickerson et al. . |
| 4,997,433 | 3/1991 | Goble et al. . |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1990 | Wiley . |
| 5,037,422 | 8/1991 | Hayhurst et al. . |
| 5,037,426 | 8/1991 | Goble et al. . |
| 5,046,513 | 9/1991 | Gatturna . |
| 5,078,730 | 1/1992 | Li . |
| 5,084,058 | 1/1992 | Li . |
| 5,087,263 | 2/1992 | Li . |
| 5,092,891 | 3/1992 | Kummer et al. . |
| 5,094,563 | 3/1992 | Carletti . |
| 5,129,902 | 7/1992 | Goble et al. . |
| 5,133,723 | 7/1992 | Li et al. . |
| 5,141,520 | 8/1992 | Goble et al. . |
| 5,147,166 | 9/1992 | Harker . |
| 5,147,362 | 9/1992 | Goble . |
| 5,152,764 | 10/1992 | Goble . |
| 5,161,916 | 11/1992 | White et al. . |
| 5,163,946 | 11/1992 | Li . |
| 5,174,087 | 12/1992 | Bruno . |
| 5,176,682 | 1/1993 | Chow . |
| 5,192,303 | 3/1993 | Gatturna et al. . |
| 5,203,787 | 4/1993 | Noblitt et al. . |
| 5,207,679 | 5/1993 | Li . |
| 5,217,486 | 6/1993 | Rice et al. . |
| 5,250,058 | 10/1993 | Miller et al. . |
| 5,263,802 | 11/1993 | Fichot et al. . |
| 5,263,991 | 11/1993 | Wiley et al. . |
| 5,266,075 | 11/1993 | Clark et al. . |
| 5,268,001 | 12/1993 | Nicholson et al. . |
| 5,300,077 | 4/1994 | Howell . |
| 5,306,290 | 4/1994 | Martins et al. . |
| 5,312,416 | 5/1994 | Spaeth et al. . |
| 5,312,422 | 5/1994 | Trott . |
| 5,312,438 | 5/1994 | Johnson . |
| 5,313,962 | 5/1994 | Obenchain . |
| 5,314,427 | 5/1994 | Goble et al. . |
| 5,314,429 | 5/1994 | Goble . |
| 5,314,433 | 5/1994 | Li . |
| 5,318,577 | 6/1994 | Li . |
| 5,324,308 | 6/1994 | Pierce . |
| 5,330,534 | 7/1994 | Herrington et al. . |
| 5,342,366 | 8/1994 | Whiteside et al. . |
| 5,350,380 | 9/1994 | Goble et al. . |
| 5,354,298 | 10/1994 | Lee et al. . |
| 5,354,300 | 10/1994 | Goble et al. . |
| 5,356,413 | 10/1994 | Martins et al. . |
| 5,358,511 | 10/1994 | Gatturna et al. . |
| 5,372,599 | 12/1994 | Martins . |
| 5,372,604 | 12/1994 | Trott . |
| 5,376,120 | 12/1994 | Sarver et al. . |
| 5,393,302 | 2/1995 | Clark et al. . |
| 5,443,482 | 8/1995 | Stone et al. . |
| 5,464,425 | 11/1995 | Skiba . |
| 5,464,427 | 11/1995 | Curtis et al. . |
| 5,486,197 | 1/1996 | Le et al. . |
| 5,500,001 | 3/1996 | Trott ........................................ 606/232 |
| 5,531,792 | 7/1996 | Huene ....................... 623/16 |
| 5,534,004 | 7/1996 | Santangelo . |
| 5,545,180 | 8/1996 | Le et al. . |

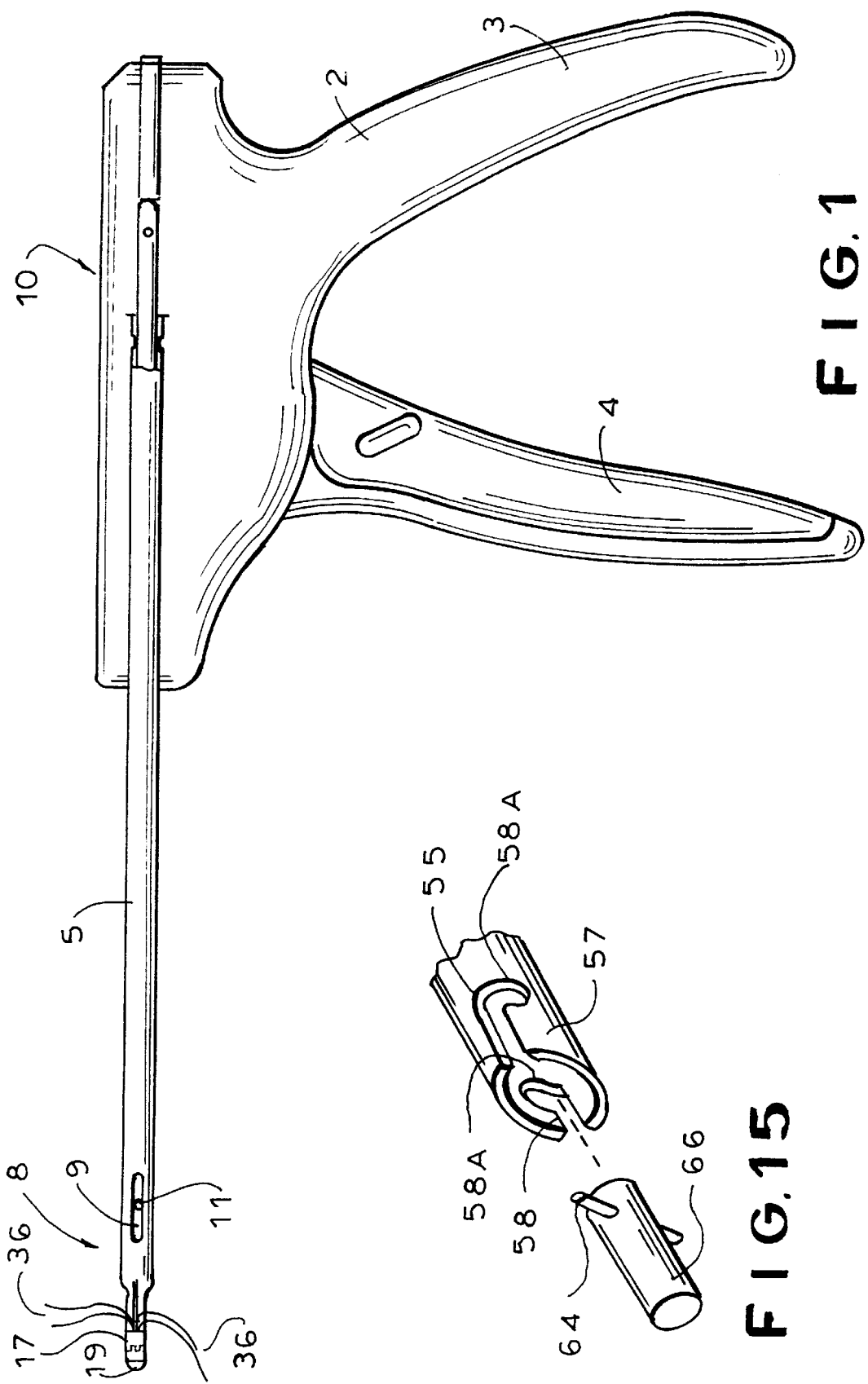

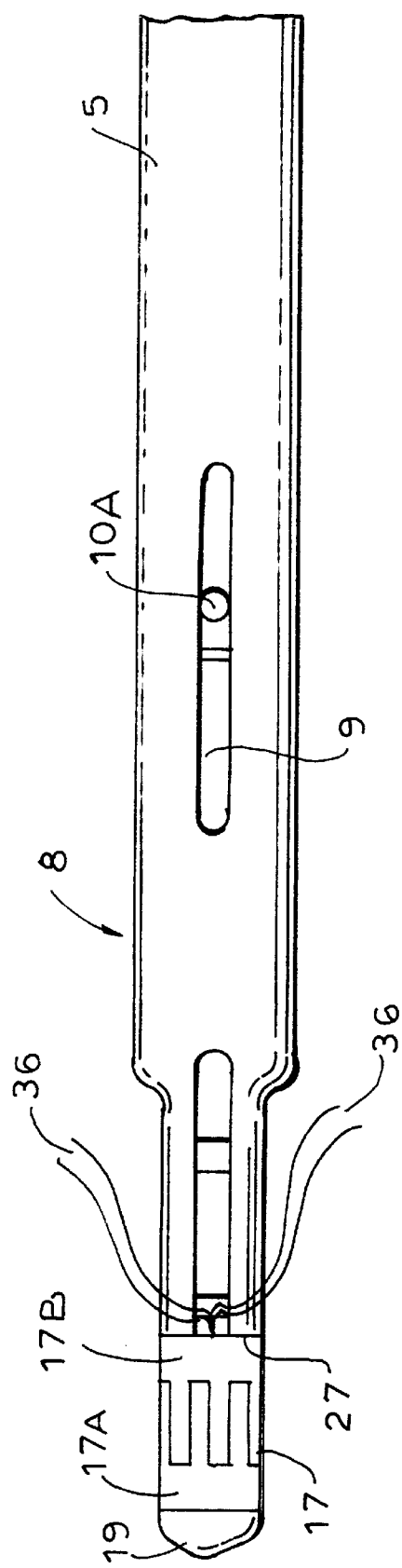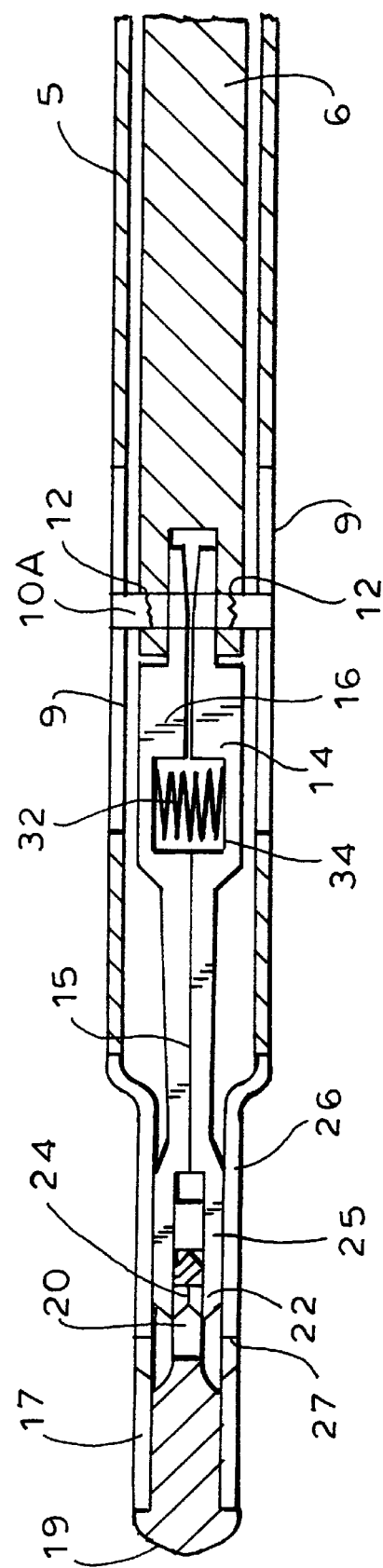

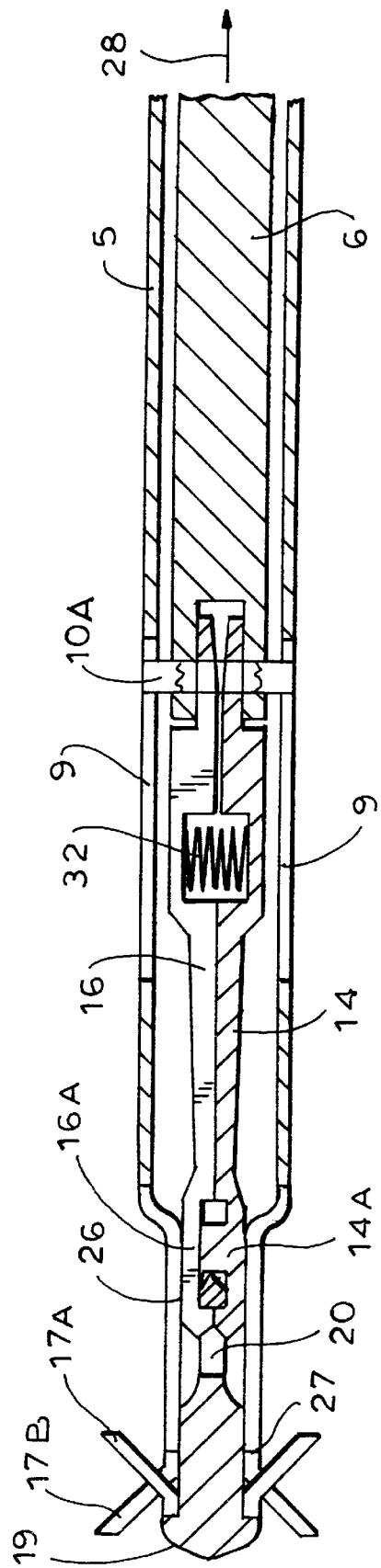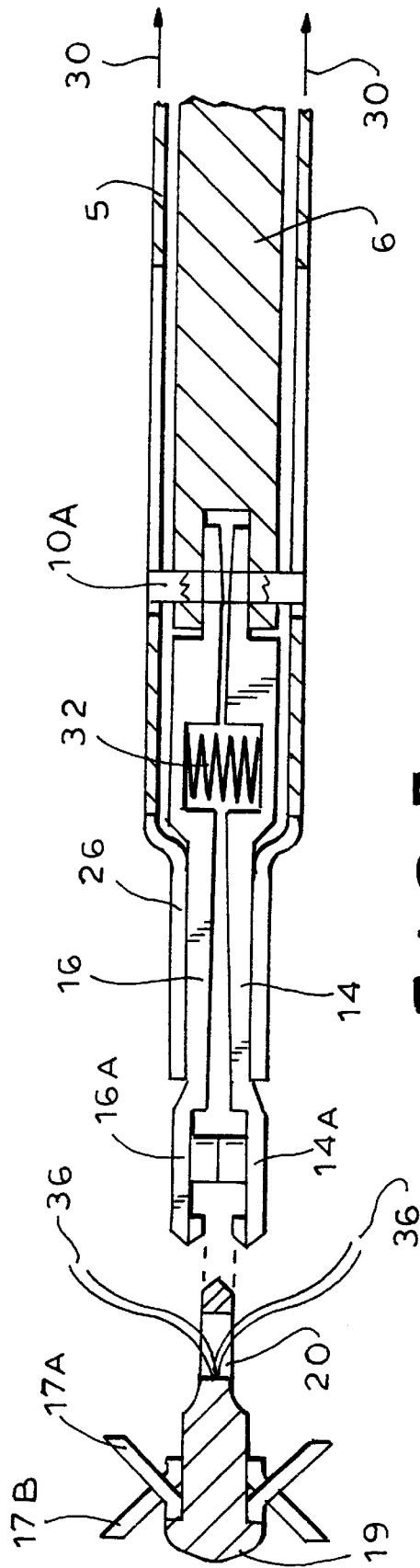

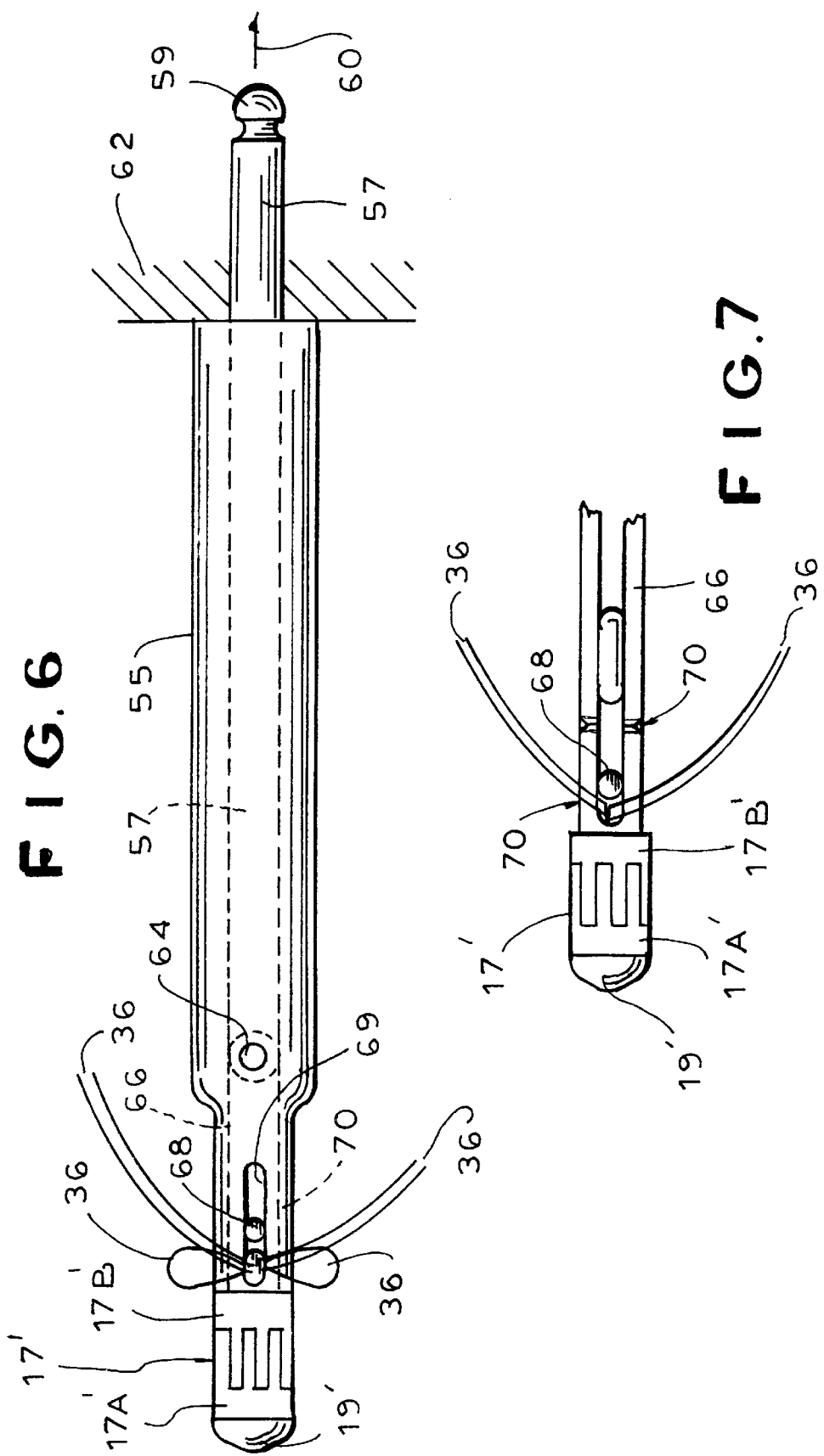

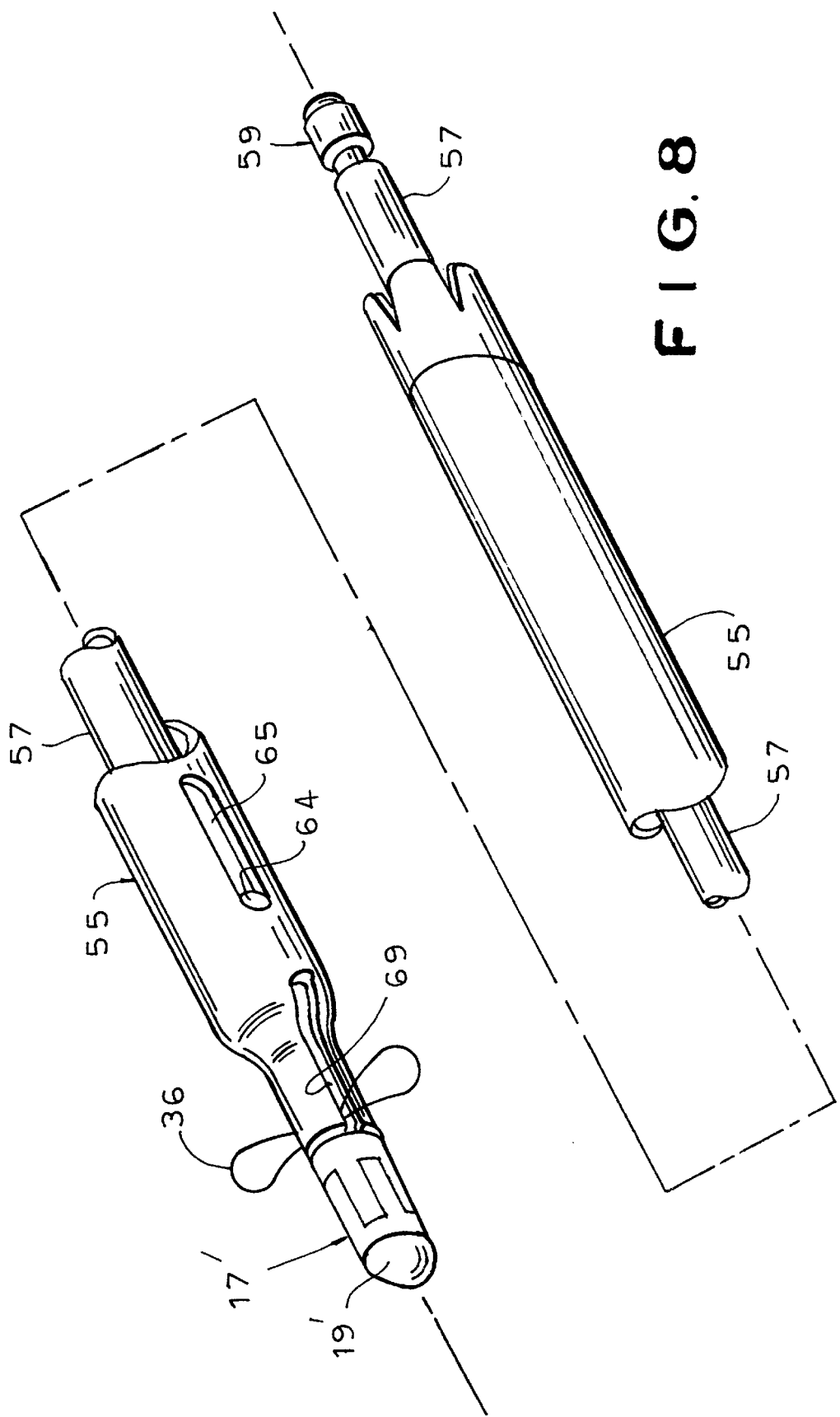

FIXATION DEVICE AND METHOD FOR INSTALLING SAME

CROSS REFERENCE TO RELATED APPLICATION

This application is a continuation-in-part of patent application Ser. No. 08/294,067 filed Aug. 22, 1994 now U.S. Pat. No. 5,645,589 and entitled "ANCHOR AND METHOD FOR SECUREMENT INTO A BORE".

BACKGROUND OF THE INVENTION

The present invention relates to fixation devices, and in particular, fixating devices for insertion into bores in materials to allow the connection of another element to the material in which the fixation is disposed. In particular, the present invention relates to a fixation device for the medical field, which can be inserted into, for example, a pre-drilled bore in bone, to allow the connection to the bone of another member, for example, a prosthetic member. Alternatively, the fixation device can have sutures attached that allow the suturing of another member to the fixation device. As an example, the fixation device of the present invention may have sutures attached thereto which allow the securement of a prosthetic device or artificial member, or a natural anatomical member, for example, ligaments, to the bone.

Although the present invention has particular application in the medical field, it is not limited thereto and may find other uses, i.e., wherever it is necessary to fasten two or more members together, especially when the members are to be secured together with fixation devices located in bore holes that are blind or open to only one side, i.e., not completely drilled through.

U.S. Pat. No. 5,268,001 to Nicholson et al. relates to a bone fastener for fixing either a suture or a rivet within a pre-drilled bone hole. In the device of that reference, the bone fastener includes an expandable sleeve having an axial bore and a pin which is forcibly insertable into the axial bore. The expandable sleeve is configured to be insertable into the bore drilled in the bone and at least a portion of the pin has an outer diameter greater than the inner diameter of at least a portion of the axial bore of the sleeve. The fastener is emplaced by inserting the sleeve into a pre-drilled hole in the bone and then forcing the pin into the axial bore of the sleeve, so that the wider portion of the pin presses outwardly against and expands the narrow portion of the sleeve, causing the sleeve to forcibly contact the walls of the bone hole and fixing the pin and sleeve firmly in place within the hole. The apparatus for emplacement of the fastener includes a holder for holding the expandable sleeve in position within the pre-drilled hole in the bone and a plunger moveable in relation to the holder for forcing the pin into the bore of the sleeve so that the pin can be forced in the axial bore without imposing substantial force toward or away from the bone. The device includes a severable attachment between the holder and the expandable sleeve which is cut by a cutting edge of a cylindrical blade. The sleeve is thereby separated from the holder body and the fully expanded and fixed fastener is freed from the insertion apparatus.

The device of the Nicholson et al. reference has several drawbacks including that a force must be applied toward the bone or member in which the fastener is being inserted. This causes greater strains than necessary to the patient because the anchor must be expanded by this pushing force, which causes undue strain on the material of the member in which the fastener is being inserted. The expandable sleeve also may not provide sufficient engaging force to secure the fastener in the bore hole in the bone because it only expands and frictionally engages in the bone without actually cutting or penetrating into the bone. Additionally, the cutting edge necessary to separate the fastener sleeve from the holder body creates additional complexity.

SUMMARY OF THE INVENTION

It is an object of the present invention to provide a fixating device.

It is yet still a further object of the present invention to provide such a fixating or fastening device which is suitable for insertion into a pre-drilled hole in a material, e.g., bone.

It is yet still a further object of the present invention to provide such a fixation or fastening device which can be used to fasten one element to another element in which the fixation or fastener device is inserted.

It is yet still a further object of the present invention to provide a fixation or fastening device which can be inserted into a material, for example, bone, to allow the connection of another member, for example, a prosthesis, or which has sutures coupled thereto for the connection of another body part, for example, ligaments, to the bone.

It is yet still a further object of the present invention to provide a fixating or fastening device which is relatively simple and convenient to use, and furthermore, which is simple to manufacture.

It is yet still a further object of the present invention to provide a fixation or fastening device which avoids the need for complicated cutting mechanisms to sever the fixation or fastening device from its insertion apparatus.

It is yet still another object of the present invention to provide an apparatus for inserting a fixation or fastener device into a pre-drilled hole in a member, for example, bone.

It is yet still a further object of the present invention to provide an apparatus for inserting a fixation or fastening device of the type generally disclosed in applicant's co-pending application Ser. No. 08/294,067 filed Aug. 22, 1994.

It is yet still another object of the invention to provide a fixation device that is conveniently loaded into its insertion apparatus.

The above and other objects of the present invention are achieved by an apparatus for inserting a fixation device securely into a bore in an element comprising a hand held device having an actuating mechanism; a longitudinally extending member coupled to the hand held device adapted to hold the fixation device at a distal end; the fixation device having a plurality of engaging members adapted to be moved outwardly when the fixation device is inserted into the bore to secure the fixation device in the bore; the extending member having an operating member coupled to the fixation device for exerting a force on the fixation device to cause the engaging members to extend outwardly to engage the wall of the bore; and the operating member being releasably coupled to the fixation device.

The objects of the present invention are furthermore achieved by a fixation device assembly for engagement by an insertion tool for inserting the fixation device assembly into a bore in a member, the assembly comprising a first member having a plurality of engaging members, the engaging members being adapted to be engaged by a cam surface to cause the engaging members to move outwardly to engage the bore in response to actuation by said insertion tool; and a second member extending longitudinally from the first member adapted to have a force releasably exerted thereon for causing the engaging members of the first member to engage the cam surface and move outwardly.

The objects of the invention are also achieved by a method for inserting a fixation device securely into a bore in an element comprising providing a hand held device having an actuating mechanism; inserting a fixation device into a longitudinally extending member of the hand held device at a distal end, the fixation device having a plurality of engaging members adapted to be moved outwardly when the fixation device is inserted into the bore to secure the fixation device in the bore; exerting a force on the fixation device with the actuating mechanism to cause the engaging members to extend outwardly to engage the wall of the bore; and releasing the fixation device from the longitudinally extending member.

Other objects, features and advantages of the present invention will become apparent from the detailed description which follows.

BRIEF DESCRIPTION OF THE DRAWINGS

The invention will now be described in greater detail in the following detailed description with reference to the drawings in which:

FIG. 1 shows an apparatus for inserting a fixation device or fastener into a pre-drilled hole in a member, for example, bone;

FIG. 2 is an enlarged view of the tip of the insertion apparatus shown in FIG. 1 with the fixation device having sutures connected thereto prior to insertion into a bore in a body member;

FIG. 3 is a cross-section through the tip of FIG. 2 rotated by 90° and prior to activation of the fixation device in a pre-drilled bore in a body member;

FIG. 4 shows a cross section of the tip of the insertion apparatus and fixation device of FIG. 3 after the fixation device has been activated into its engaging state;

FIG. 5 shows a cross section of the tip of the insertion apparatus and the fixation device after the fixation device has been separated from the insertion apparatus;

FIG. 6 shows a second embodiment of the present invention showing a detachable holding device for insertion of a variant of the fixation device of the present invention which has a frangible connecting point to the holding device so that the fixation device can be separated from the holding device once insertion is complete;

FIG. 7 shows the fixation device according to the device of FIG. 6 with the cylindrical cover of the holding device removed, for clarity;

FIG. 8 is a perspective view of the embodiment shown in FIG. 6;

FIG. 15 shows one embodiment of a detachable coupling device coupling a fixation device assembly to its insertion device.

DETAILED DESCRIPTION OF EMBODIMENTS OF THE INVENTION

Figure 12:
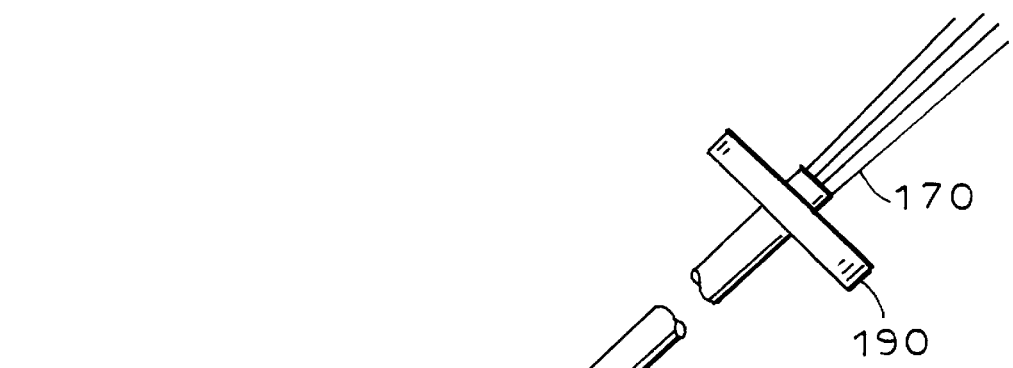
FIGS. 12, 13 and 14 show one embodiment of the fixation device disclosed in Applicant's co-pending application Ser. No. 08/294,067, generally showing the structure of the fixation device employed in this application.
Figure 13:
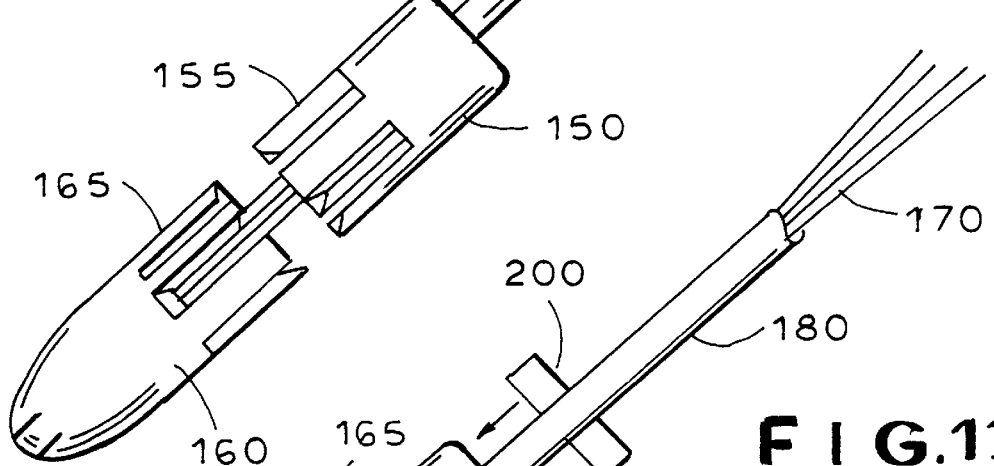
Figure 14:
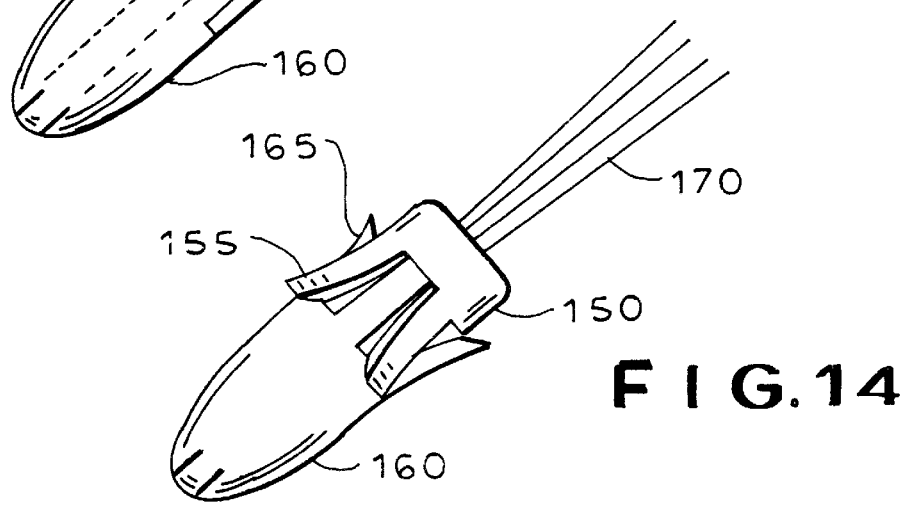

With reference now to the drawings, FIGS. 12, 13 and 14 generally show the type of fixation device which is described in Applicant's co-pending application Ser. No. 08/294,067 filed Aug. 22, 1994 and to which the present application generally relates and of which the present application is an improvement thereon.

FIG. 12 generally shows the type of fixation device described in the instant application comprising a two-piece fastener comprising pieces 150 and 160, each of which has a group of longitudinally directed fingers 155 and 165 which are distributed circumferentially around the respective fasteners 150, 160. The fingers 155 and 165 interdigitate, as shown in FIG. 13, which shows the fixation device prior to insertion. Once inserted into a bore, for example, a bore in bone, the two portions 150 and 160 of the fastener are moved relatively together, causing the interdigitated fingers to expand outwardly against each other due to the cam surfaces on the opposite member, as shown in FIG. 14. The extended fingers securely engage the walls of the bore in which the fixation device is disposed, providing a secure attachment point. The fingers 155 and 165 may have sharp tips for digging into the wall of the bore hole. The insertion tool, which is shown schematically in these Figures and designated with the reference numerals 180, 190 and 200, is then removed, leaving the fixation device in place and the sutures 170 extending from the bore in which the fixation device is disposed. The fixation device shown in FIGS. 12, 13 and 14 and to be described generally herein may be made of any biocompatible material, for example, a suitable plastic material or a suitable biocompatible metal, for example, a stainless steel. Although sutures are shown connected to the anchor in FIGS. 12 to 14, the fixation device could also have any other suitable attaching means, e.g., a threaded hole or post for the attachment of some other member, e.g., a prosthetic device.

In the embodiment shown in FIGS. 12, 13 and 14, the two members 150 and 160 of the fastener are drawn together by providing a force on the collar 200 while holding member 160 fixed, which forces the member 150 toward the member 160, thereby flexing and extending the fingers 155 and 165 radially outwardly and each pointed in opposite directions. The extended fingers frictionally grasp the bore in which they are inserted or cut into the interior surface of the bore to hold the fastener securely therein. The fingers 155 and 165 may be formed such that their tips are sharpened, to facilitate the securement of the fixation device in the bore. The extension of the fingers 155 and 165 pointed along the two opposite directions provides a secure attachment of the fastener in the bore, i.e., the extension of the fingers 155 and 165 pointed along two opposite directions both prevents the fastener from moving further inwardly into the bore (if the bore has a further extension), and prevents the fixation device from being pulled out of the bore.

The present invention is an improvement on the fixation device and insertion devices shown generally in FIGS. 12, 13 and 14 and described in Applicant's copending application.

Figure 3A:
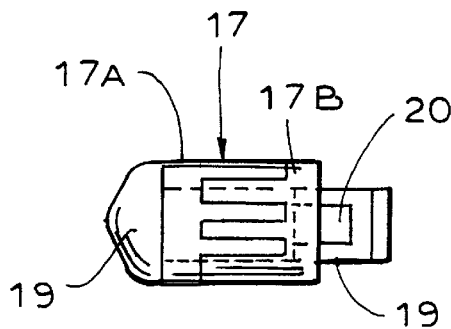
FIG. 3A is a side view of the fixation device shown in FIG. 3.

As shown in FIGS. 1–5, which show an embodiment of a fixation device and its insertion device according to the present invention, the invention generally comprises an insertion apparatus generally designated 10 which may comprise an insertion device 2 which includes a pistol-like grip 3 and an actuating lever 4. Extending from the body of the insertion gun 2 is a cylinder 5 shown in greater detail in FIGS. 2, 3, 4 and 5. The cylinder 5 provides a housing for a shaft 6. Both the cylinder and shaft are mechanically operated by the lever 4. The shaft 6 is coupled to the actuating lever 4 such that it is slidable within the cylindrical sleeve 5. At a distal end 8, the cylindrical sleeve includes a longitudinally extending slide opening 9 having a pin 10 slidable therein. The pin 10 is fixed in bores 12 provided in the shaft 6. The pin 10 is tightly fitted into shaft 6 and slidable through members 14 and 16 of a forceps, generally designated 15. At the distal end of the forceps 15, a fixation device 17 of the type generally described in applicant's co-pending application is disposed. The fixation device is shown in FIG. 3a in a view corresponding to that shown in FIG. 2. The fixation device 17 includes two sections 17A and 17B having interdigitated longitudinally-extending engaging members of fingers, as described with respect to FIGS. 12, 13 and 14. The fingers can take any shape so long as they provide the function of engaging into a borehole once extended outwardly. Extending through the interior of the fixation device 17 is a bolt 19, which has an opening 20 therein that receives the engaging prongs 22 and 24 of the respective forceps members 14 and 16. As shown in FIG. 3, the forceps 15 is kept in a closed condition (holding fixation device 17) against the action of a spring 32 by virtue of its engagement at its head end 25 in a reduced diameter portion 26 of the cylinder 5.

In order to operate the device and insert the fixation device 17 into a pre-drilled hole in a member, for example, a hole in bone, the user grasps the pistol-like insertion device 2 and inserts the tip, having the fixation device 17, into the opening in the bone. The lever 4 is then operated, pulling the lever toward the pistol grip 3. This causes the shaft 6 to move in the direction of arrow 28 as shown in FIG. 4. The pin 10 slides in the longitudinally extending hole 9 as shown in FIG. 4. The pin 10 is prevented from moving further by the limit stops provided by the guide opening 9. The movement of shaft 6 has the effect of moving bolt 19 coupled to it in the same direction, causing fixation device member 17B to abut the cylinder 5 at 27. The further movement of shaft 6 and thus bolt 19 then causes members 17A and 17B to move toward each other, thereby causing the fingers attached to members 17A and 17B to move outwardly, as shown in FIG. 4, into engagement with the wall of the bore hole, not shown. The orientation of the fingers may be somewhat exaggerated in FIGS. 4 and 5 for clarity. The fixation device 17 is now securely emplaced in the bore hole, not shown, although still attached to the insertion apparatus.

When the pin 10 reaches the extent of its travel, upon further actuation of the lever 4, cylinder 5 is then actuated to cause it to move in the direction of arrows 30 (FIG. 5). Prior to movement of the cylinder 5, the ends 14A and 16A of the forceps portions 14 and 16 remain in the portion 26 of reduced diameter of the cylinder 5, as shown in FIG. 4. Upon further movement of the operating lever 4, and thus movement of the cylinder 5, the cylinder 5 moves in the direction of arrows 30, causing the reduced diameter portion 26 to ride off the portions 14A and 16A of the respective forceps portions 14 and 16, as shown in FIG. 5. This allows spring 32 under compression disposed in an opened area 34 between the forceps members 14A and 16A, to expand, forcing the forceps portions 14 and 16 away from each other. This frees the fastener 17, with the bolt 19 attached, from the forceps 15 of the insertion device. The insertion device can now be removed, leaving the fastener 17 and bolt 19 securely in place in the bore in the bone. The fastener 17 and bolt 19, with sutures, generally designated 36, attached, is now securely embedded in the bore in the bone by virtue of the extension of the fingers of members 17A and 17B, which now firmly grasp the opening in the bone. Depending upon the material in which it is inserted, and the shape of the fingers on fastener members 17A and 17B, the fingers may actually cut into the material in which they are secured or may provide a frictional engagement. Also, the bolt 19 is securely held in the members 17A and 17B due to the compression of the inner diameter of the members 17A and 17B caused by the force of the extended finger impacting against the wall of the bore in the bone.

The embodiment of FIGS. 1–5 shows a fixation device or fastener 17 and separate bolt 19. The bolt 19 can be made part of one of the portions 17A of the fixation device or it can be made, as shown, as a separate part. Furthermore, the sutures 36 may be fastened to the bolt 19 or may be fastened to the portions 17A. Additionally, the fastener shown in FIGS. 1–5 shows sutures attached thereto which can be used, for example, to attach a ligament or other member to bone. The fastener 17 can just as well be used as a rivet or screw attachment in which case it may have a screw or other hole therein or have a post for attachment of another member thereto, for example, a prosthesis.

Figure 9:
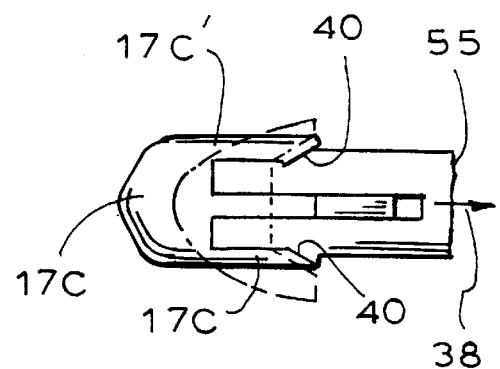
FIG. 9 is a side view of a third embodiment of the fixation device of the present invention.

Although the fastener shown in FIGS. 1–5 has portions 17A and 17B which have fingers that point in opposite directions, and which provide two way securement of the fixation device in the member in which it is secured, the fastener may have fingers which extend only in one direction, and preferably in a direction preventing pulling of the fastener out of the bore. This is shown, for example, in FIG. 9, which shows a fastener 17C which includes fingers 17C'. The fastener 17C is caused to move to the position shown in phantom in FIG. 9, thereby embedding itself in a bore in a member in which it is secured when a pulling force 38 is applied. Unlike the fastener 17 shown in FIGS. 1–5, however, because there are no opposed fingers pointing in the opposite direction, a cam surface 40 on cylinder 55 may be provided so that the fingers 17C' can be forced to move outwardly. Thus, when pulling force 38 is exerted on the fastener 17C, it moves in the direction of arrow 38 while simultaneously, the engagement of each finger 17C' against the cam surfaces 40 causes the fingers to move outwardly into engagement with the bore hole. Alternatively, the cam surface can be located on the fixation device, instead of on cylinder 55. Further, the cylinder 55 may also subject the fixation device to a pushing force, instead of a pulling force to fasten the fixation device.

FIGS. 6, 7 and 8 show an alternative embodiment of the present invention. In this embodiment, the insertion device includes a cylinder 55 having a rod 57 slidable therein. The rod 57 is provided with a graspable end 59 which is grasped by an insertion device 2 of the type shown in FIG. 1, and not shown in detail. The insertion device of the type shown in FIG. 1 pulls the shaft 57 in the direction of arrow 60 while simultaneously holding the cylinder 55 in position, as shown by the shading 62 in FIG. 6. The shaft 57 near its distal end has a bore therethrough in which a pin 64 is inserted. The pin 64 couples the shaft 57 to a coupling shaft 66. The pin 64 is slidable in a longitudinal opening 65 in cylinder 55. Another pin 68 slidably engages in an opening 69 in the shaft 66, which may be formed integrally with bolt 19'. The bolt 19' extends through the interior of fixation device 17' which is formed from two portions 17A' and 17B', as in the embodiment of FIGS. 1–5. Sutures 36 may be attached to the bolt 19 or the fastener 17'.

Upon the application of force in the direction of arrow 60 to shaft 57, fixation device 17' is drawn toward cylinder 55. Upon making contact with cylinders 55 at 56, member 17B' is prevented from moving. Member 17A', due to the continuing movement of bolt 19', however, is forced into member 17B', causing the fingers of members 17A' and 17B' to move outwardly, securing the fixation device 17' in the bore hole.

Unlike the embodiment shown in FIGS. 1–5, however, the shaft 66 includes a frangible connection 70 which comprises a portion of the shaft 66 having an area of increased weakness, e.g., a groove or slit 70 which causes the shaft 66 to break upon the application of a specified pressure, in the embodiment shown, a tensile force. The tensile force is greater than the force necessary to form the fixation device 17' into its engaging state. The frangible connection point 70 may be, for example, a reduced thickness area of the fork 66 which is designed to rupture at the specified pressure. Upon rupturing, the insertion device may be removed from the fixation device, thereby leaving the fixation device, with the fingers extended and engaging securely in the bore hole, and the bolt 19' in place in the bore in the member in which the fastener is secured.

FIG. 15 shows one embodiment for attaching shaft 66 to shaft 57 via pin 64. Preferably this attachment is releasable so the user can conveniently load a fixation device 17', with bolt 19' having shaft 66 attached, as an assembly to the insertion device. As shown in FIG. 15, the releasable coupling may take the form of a bayonet coupling, although other equivalent convenient releasable coupling devices can be employed. To insert the fixation device assembly into the insertion device, pin 64 is first guided through an opening 69 in shaft 66, slid into the bore of the cylinder 55 into the slots 58 while also guided in slot 65, shaft 57 is then turned to secure shaft 66 to shaft 57 with pin 64 being seated in portion 58A of the bayonet slots 58.

Figure 10:
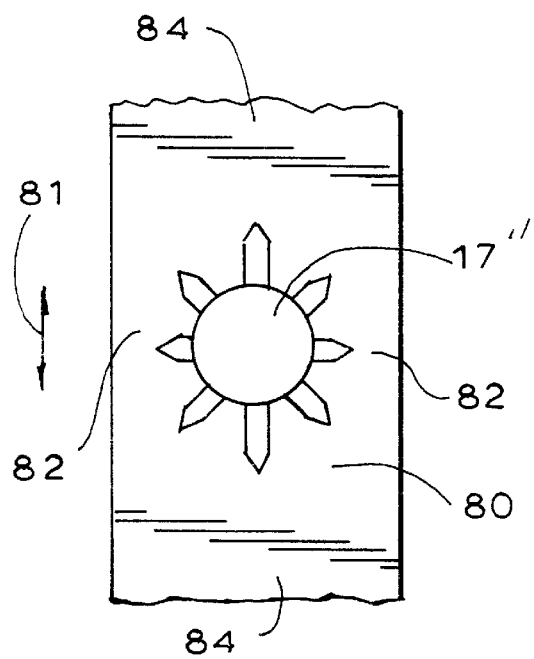
FIG. 10 shows an fixation device according to the present invention which has been modified to reduce the amount of stress that the fixation device provides to the member in which it is secured.
Figure 11:
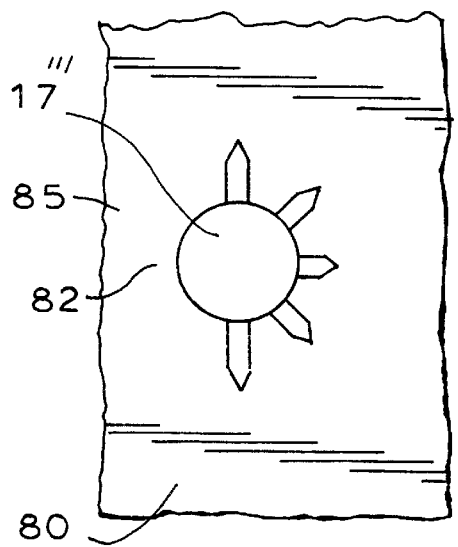
FIG. 11 shows another modification of the fixation device according to the present invention.

FIGS. 10 and 11 show alternative embodiments of the fixation devices shown both in FIGS. 1–5 and in FIGS. 6–9. FIGS. 10 and 11 show the fixation devices (with engaging finger elements in extended positions and exaggerated for effect) in place in bores in materials 80. In the example shown in FIG. 10, the material 80 is a longitudinally extending object extending in a direction shown by the arrow 81. It is relatively narrow and accordingly, it is important that the material 80 not be stressed along the thin portions 82 on either side of the bore hole into which the fastener 17" is inserted. Accordingly, the fingers of fastener 17" near the portions 82 can be made shorter so that they reduce the stress applied to the portions 82 of the material. As shown, the fingers near the stronger areas 84 may be made longer.

FIG. 11 shows another embodiment in which a bore is made close to a side 85 of the material 80. In this case, no fingers are provided on the side of the fixation device 17'" near the weaker area 82. Thus, it is not necessary that the fingers be spaced equiangularly about the fixation device. Accordingly, the fastener of the present invention may be adapted, as necessary to the particular application, thereby to prevent damage to the underlying material 80 when there is a likelihood that the stress caused by the fixation device may break the material into which it is inserted. In addition to changing the length and spacing of selected fingers, other modifications can be made to the fixation device depending on the circumstances.

The fixation device of the present invention may be provided to users as a one-time use-disposable assembly. For example, in the embodiment of FIGS. 1–5, the fixation device assembly comprising fixation device 17 and a bolt 19 can be provided to users for use with the insertion apparatus.

In the embodiment of FIGS. 6–8, the assembly comprising only the fixation device 17' and bolt 19' including coupling shaft 66 with frangible connection 70 can be provided as a unit. Alternatively, the assembly comprising what is shown in FIGS. 6 or 8 can be provided as a unit, i.e., bolt 19' with shaft 66, fixation device portion 17', cylinder 55 and shaft 57. This entire unit can be packaged as a one-use disposable member. After the frangible connection 70 ruptures leaving the fixation device fixed in place, the entire assembly is discarded and a new one inserted into the hand held insertion device. The ball-shaped end 57 provides a snap-fit into the insertion device. In this disposable embodiment, the bayonet connection of FIG. 15 is unnecessary.

As an additional modification, the bolt 19, 19' can be made integral with or screwed into or otherwise secured to member 17A, 17A', in which case the head of the bolt can be eliminated.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Apparatus including a fixation device and a device for inserting the fixation device securely into a bore in an element, the apparatus comprising:

a hand held device having an actuating mechanism;

a longitudinally extending member coupled to the hand held device adapted to hold the fixation device at a distal end;

a fixation device having a plurality of longitudinally extending engaging members adapted to be moved outwardly when the fixation device is inserted into the bore to secure the fixation device in the bore;

the extending member having an operating member adapted to be coupled to the fixation device for exerting a force on the fixation device tending to cause the engaging members to extend outwardly to engage the wall of the bore;

the operating member being releasably coupled to the fixation device;

the extending member comprising a cylinder and the operating member comprising a shaft disposed concentrically in the cylinder, the operating member being coupled to the fixation device for exerting an axial force on the fixation device without rotation of the operating member to cause the engaging members of the fixation device to extend outwardly;

the fixation device further comprising two parts, each having engaging members extending in one of two opposite directions, one of said parts being in engagement with an abutment surface of the cylinder to prevent movement of the part, the engaging members of the two parts being interdigitated but not necessarily on a one-to-one ratio of interdigitated engaging members and the other part being acted on by said operating member, each part having cam surfaces thereon for causing opposed engaging members of the other part to extend outwardly in response to the force applied by the operating member.

2. The apparatus of claim 1, wherein the operating member terminates in a forceps, the forceps releasably grasping the fixation device.

3. The apparatus of claim 2, wherein the cylinder is in slidable engagement with a surface of the forceps to keep the forceps in engagement with the fixation device and the cylinder is movable with respect to the forceps to cause the forceps to release the fixation device after the engaging members of the fixation device have extended outwardly to secure the fixation device in the bore.

4. The apparatus of claim 3, wherein the forceps comprise two opposed members for engaging the fixation device with a spring disposed therebetween to bias the opposed members away from each other to release the fixation device.

5. The apparatus of claim 4, wherein the shaft is adapted to move the forceps a preset longitudinal distance and the cylinder comprises a section slidably in contact with a corresponding portion of the forceps to hold the forceps in a state of engaging the fixation device, the cylinder being thereafter movable longitudinally so that the section in slidable contact with the forceps moves off the corresponding portion of the forceps thereby to release the forceps from engaging the fixation device.

6. The apparatus of claim 5, wherein the fixation device comprises a center member having an engagement point for engagement by the forceps.

7. The apparatus of claim 6, wherein the engagement point comprises an opening in the center member.

8. The apparatus of claim 6, wherein the center member is integral with at least a portion of the fixation device.

9. The apparatus of claim 7, wherein the center member is a separate part from a fixation device portion having the engaging members.

10. The apparatus of claim 1, wherein at least one of the engaging members is of a different length than the other engaging members.

11. The apparatus of claim 1, wherein the engaging members are equiangularly spaced about the circumference of the fixation device.

12. The apparatus of claim 1, wherein the engaging members are not equiangularly spaced about the circumference of the fixation device.

13. The apparatus of claim 1, wherein the operating member terminates in a coupling member coupling the operating member to the fixation device, the coupling member having a frangible connection whereby when a preset force in the coupling member is exceeded, the frangible connection breaks, releasing the fixation device from the operating member.

14. The apparatus of claim 13, wherein the frangible connection comprises a portion of said coupling member of weakened condition.

15. The apparatus of claim 14, wherein the frangible connection comprises an area of reduced thickness in said coupling member.

16. The apparatus of claim 15, wherein the area of reduced thickness comprises a groove or slit.

17. The apparatus of claim 13, wherein the coupling member is coupled to the shaft with a releasable connection.

18. The apparatus of claim 17, wherein the releasable connection comprises a bayonet connection.

19. The apparatus of claim 1, wherein the fixation device is adapted to connect to another member.

20. The apparatus of claim 19, wherein the fixation device includes a connector for attaching to another member.

21. Apparatus including a fixation device and a device for inserting the fixation device securely into a bore in an element, the apparatus comprising:

a hand held device having an actuating mechanism;

a longitudinally extending member coupled to the hand held device adapted to hold the fixation device at a distal end;

a fixation device having a plurality of longitudinally extending engaging members adapted to be moved outwardly when the fixation device is inserted into the bore to secure the fixation device in the bore;

the extending member having an operating member adapted to be coupled to the fixation device for exerting a force on the fixation device tending to cause the engaging members to extend outwardly to engage the wall of the bore;

the operating member being releasably coupled to the fixation device;

the extending member comprising a cylinder and the operating member comprising a shaft disposed concentrically in the cylinder, the operating member being coupled to the fixation device for exerting an axial force on the fixation device to cause the engaging members of the fixation device to extend outwardly;

the fixation device further comprising two parts, each having engaging members extending in one of two opposite directions, one of said parts being in engagement with an abutment surface of the cylinder to prevent movement of the part, the engaging members of the two parts being interdigitated but not necessarily on a one-to-one ratio of interdigitated engaging members and the other part being acted on by said operating member, each part having cam surfaces thereon for causing opposed engaging members of the other part to extend outwardly in response to the force applied by the operating member; and further wherein the fixation device has a suture connected thereto.

22. A fixation device assembly for engagement by an insertion tool for inserting the fixation device assembly into a bore in a member, the assembly comprising:

a first member having a plurality of engaging members, the engaging members being adapted to be engaged by a cam surface to cause the engaging members to move outwardly to engage the bore in response to actuation by said insertion tool;

a second member extending longitudinally from the first member adapted to have a force releasably exerted thereon for causing the engaging members of the first member to engage the cam surface and move outwardly; and further comprising a third member having a plurality of engaging members extending oppositely to the engaging members of said first member, the engaging members of the first and third members being interdigitated, the cam surface for causing each respective engaging member to extend outwardly comprising a surface of the respective first and third members disposed opposite each respective engaging member; and wherein one of the first, second and third members has sutures connected thereto.

23. A fixation device assembly for engagement by an insertion tool for inserting the fixation device assembly into a bore in a member, the assembly comprising:

a first member having a plurality of engaging members, the engaging members being adapted to be engaged by a cam surface to cause the engaging members to move outwardly to engage the bore in response to actuation by said insertion tool;

a second member extending longitudinally from the first member adapted to have an axial force releasably exerted thereon for causing the engaging members of the first member to engage the cam surface and move outwardly;

a third member having a plurality of engaging members extending oppositely to the engaging members of said first member, the engaging members of the first and third members being interdigitated, the cam surface for causing each respective engaging member to extend outwardly comprising a surface of the respective first and third members disposed opposite each respective engaging member; and further comprising a fourth member, the fourth member comprising a cylinder having a concentric shaft disposed therethrough, the concentric shaft non-rotationally providing the axial force to said second member, and further wherein the cylinder abuts one of said first and third members to prevent said one member from moving when said force is applied to the other of said first and third members.

24. The assembly of claim 23, wherein the concentric shaft has a snap-in end for removably attaching to the insertion tool.

25. Apparatus including a fixation device and a device for inserting the fixation device securely into a bore in an element, the apparatus comprising:

a hand held device having an actuating mechanism;

a longitudinally extending member coupled to the hand held device adapted to hold the fixation device at a distal end;

a fixation device comprising a generally cylindrical element having a plurality of longitudinally extending engaging members adapted to be moved generally radially outwardly when the fixation device is inserted into the bore to secure the fixation device in the bore;

the extending member having an operating member adapted to be coupled to the fixation device for exerting a force on the fixation device tending to cause the engaging members to extend generally radially outwardly to engage the wall of the bore;

the operating member being releasably coupled to the fixation device;

the extending member comprising a cylinder and the operating member comprising a shaft disposed concentrically in the cylinder, the operating member being coupled to the fixation device for exerting an axial force on the fixation device without rotation of the operating member to cause the engaging members of the fixation device to extend generally radially outwardly;

the engaging members of the cylindrical element of the fixation device having an initial undeployed position extending in a direction along the longitudinal axis of the longitudinally extending member, said cylindrical element being acted on by said operating member, said engaging members having proximal surfaces abutting against a cam surface on said cylinder for causing said engaging members to move to a deployed position wherein the engaging members extend generally radially outwardly at an angle to the longitudinal axis in response to the force applied by the operating member.

26. The apparatus of claim 25, further wherein the fixation device has a suture connected thereto.

* * * * *